(12) United States Patent
Shah et al.

(10) Patent No.: US 10,814,139 B2
(45) Date of Patent: Oct. 27, 2020

(54) LOW ENERGY PHOTONIC LASER DEVICE

(71) Applicant: Advino Technologies, Ahmedabad (IN)

(72) Inventors: Kevin R. Shah, Ahmedabad (IN); Dharmesh O. Savani, Ahmedabad (IN); Sanandan Sudhir, Ahmedabad (IN); Mahaan Ghose, Ahmedabad (IN)

( * ) Notice: Subject to any disclaimer, the term of this patent is extended or adjusted under 35 U.S.C. 154(b) by 212 days.

(21) Appl. No.: 16/304,524

(22) PCT Filed: May 26, 2017

(86) PCT No.: PCT/IB2017/053108
§ 371 (c)(1),
(2) Date: Nov. 26, 2018

(87) PCT Pub. No.: WO2017/203476
PCT Pub. Date: Nov. 30, 2017

(65) Prior Publication Data
US 2019/0299023 A1    Oct. 3, 2019

(30) Foreign Application Priority Data

May 26, 2016  (IN) .............................. 201621018170
May 25, 2017  (IN) .............................. 201721018464

(51) Int. Cl.
*A61N 5/067* (2006.01)
*A61N 1/36* (2006.01)
(Continued)

(52) U.S. Cl.
CPC ............. *A61N 5/0616* (2013.01); *A61N 1/00* (2013.01); *A61N 1/328* (2013.01);
(Continued)

(58) Field of Classification Search
CPC .................................. A61N 1/26; A61N 1/328
See application file for complete search history.

(56) References Cited

U.S. PATENT DOCUMENTS

| | | | | |
|---|---|---|---|---|
| 1,011,498 A | * | 12/1911 | Saphiloff | ........... A61H 15/0092 601/119 |
| 1,501,342 A | * | 7/1924 | Hoard | ................ A61H 15/0092 601/123 |

(Continued)

OTHER PUBLICATIONS

International Search Report and Written Opinion dated Aug. 23, 2017, in corresponding PCT international patent application No. PCT/IB/2017/053108, International Filing Date May 26, 2017.

*Primary Examiner* — Kennedy Schaetzle
(74) *Attorney, Agent, or Firm* — David Postolski, Esq.; Gearhart Law LLC

(57) ABSTRACT

A multifunctional therapeutic device for providing therapy to human body is disclosed. The device incorporates means for any one or combination of different therapies, namely electric pulse therapy, UV therapy, Low energy laser therapy, and heat therapy, that can be operated individually or simultaneously as per requirement. The device is double ended with each end incorporating capability to impart each of the therapies either individually or in combination. One end is configured for therapy to a smaller area, and the other end configured to provide therapy to a larger area of human body. Two identical laser devices are used along with converging and diverging coupling systems to focus laser to a smaller or larger area. Device includes a single display that rotates the displayed data depending on which side is being used; and includes a hand wheel for adjusting intensity of therapy that allows ambidextrous application.

18 Claims, 15 Drawing Sheets

(51) Int. Cl.
  *A61N 5/06* (2006.01)
  *B23K 26/00* (2014.01)
  *A61N 5/00* (2006.01)
  *A61N 1/00* (2006.01)
  *A61N 1/32* (2006.01)
  *A61B 18/00* (2006.01)

(52) U.S. Cl.
  CPC ........... *A61N 1/36014* (2013.01); *A61N 5/00* (2013.01); *B23K 26/0096* (2013.01); *A61B 2018/00452* (2013.01); *A61N 2005/067* (2013.01); *A61N 2005/0644* (2013.01); *A61N 2005/0661* (2013.01)

(56) References Cited

U.S. PATENT DOCUMENTS

| | | | | |
|---|---|---|---|---|
| 2,653,598 | A * | 9/1953 | Torino | A46B 15/0055 601/141 |
| 4,033,356 | A * | 7/1977 | Hara | A61N 1/0452 607/152 |
| 5,024,236 | A * | 6/1991 | Shapiro | A61N 5/0619 128/907 |
| 5,304,207 | A * | 4/1994 | Stromer | A61N 1/32 607/145 |
| 8,784,345 | B2 * | 7/2014 | Peddicord | A61H 19/34 601/46 |
| 8,844,543 | B2 * | 9/2014 | Bickford | A45D 40/28 132/320 |
| 10,064,701 | B1 * | 9/2018 | Kashi | A61C 5/62 |
| 2006/0058714 | A1 * | 3/2006 | Rhoades | A45D 34/04 601/73 |
| 2011/0032960 | A1 | 2/2011 | Gerlitz | |
| 2011/0230701 | A1 * | 9/2011 | Simon | A61N 1/40 600/9 |
| 2012/0253245 | A1 * | 10/2012 | Stanbridge | A61H 23/008 601/101 |
| 2013/0048011 | A1 * | 2/2013 | Bickford | A45D 40/28 132/320 |
| 2015/0112411 | A1 | 4/2015 | Beckman et al. | |
| 2017/0304654 | A1 * | 10/2017 | Blanche | A61H 23/0245 |
| 2020/0069936 | A1 * | 3/2020 | Wang | A46B 15/0022 |

* cited by examiner

LOW ENERGY PHOTONIC LASER DEVICE

This application is a 371 National Phase of PCT International Application Number PCT/IB2017/053108, filed on May 26, 2017, titled "LOW ENERGY PHOTONIC LASER DEVICE", which claims priority from Indian provisional Applications 201621018170 filed on May 26, 2016 and 201721018464 filed on May 25, 2017, the entire contents of which are incorporated herein by reference.

TECHNICAL FIELD

The present disclosure relates to the field of medical devices. More particularly, the present disclosure relates to a multifunction low energy photonic laser treatment device.

BACKGROUND

Background description includes information that may be useful in understanding the present invention. It is not an admission that any of the information provided herein is prior art or relevant to the presently claimed invention, or that any publication specifically or implicitly referenced is prior art.

In the past few decades, a rapid development has been seen in field of medical instruments, devices, technology, and treatment. Low energy photonic laser treatment is one of the improved ways for treating a number of diseases including urology, eyes related issues, and for treatment of malignant tumors etc.

With latest development and modernization in low energy photonic laser technology, some of the devices that have been developed are being used for treatment of pain of internal stressed tissues. Existing technologies still have some limitations that reduce their utility such as in case of low energy photonic laser devices.

United States Patent Application 20110112613 discloses a low level laser therapy (LLLT) system and device with a laser diode, a momentary switch, and a clip device configured to attach to the LLLT device and to press the momentary switch while attached, causing the LLLT device to activate the laser diode. A LLLT device includes a laser diode, a front end from which light radiates when the laser diode is activated, and an eye safety mechanism at the front end. The LLLT device is configured to activate the laser diode when the front end is pressed.

U.S. Pat. No. 6,312,451 discloses a low level laser therapy apparatus for treatment of various tissue injuries. In one embodiment, the apparatus includes a handheld laser probe coupled to a control unit for selecting and controlling laser energy dosage from about 1 joule/point to about 10 joules/point. The apparatus emits laser energy at a wavelength from about 630 nm to about 904 nm, with a mean power output of between about 100 mW to about 500 mW. The apparatus further includes an access control mechanism to limit operability to trained personnel.

However, both the devices can be operated from one side only, which restricts the operating area, and a large time is required for covering a larger area because the operating area is fixed, and therefore one has to cover larger areas only by covering smaller areas one by one. Also, if a treatment is required at a particular smaller area or at a larger area at the same time, one cannot focus on both the areas simultaneously because of the fixed operating area of the existing device, and therefore for covering larger as well smaller area together, separate low energy photonic laser devices are required. Besides, they provide only laser therapy, and therefore when a different therapy is to be applied a different device would be required.

Therefore, there is a need in the art for a single device that can be operated from dual sides, and can focus on smaller as well as larger areas at once or one by one for treatment. It would be further advantageous if the device could provide a combination of different therapies such as electric pulse therapy, U.V. therapy, Low energy laser therapy, and heat therapy to a human body part, either individually or in any combination for a holistic approach.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

OBJECTS OF THE INVENTION

A general object of the present disclosure is to provide a cost effective alternative for individual devices for individual therapies which if summed up are much more expensive.

An object of the present disclosure is to provide a multifunctional therapeutic device that incorporates flexibility to enable application to a large area or small area of human body depending on requirement.

An object of the present disclosure is to provide a double ended therapeutic device that cater to small area and large area respectively.

Another object of the present disclosure is to provide a multifunctional therapeutic device that enables a user to use more than one therapy in different combinations for more efficient healing.

Another object of the present disclosure is to provide a multifunctional therapeutic device that incorporates means for any one or a combination of different therapies such as electric pulse therapy, U.V. therapy, Low energy laser therapy, and heat therapy to a human body part, thus making it a holistic therapeutic device.

Another object of the present disclosure is to provide a therapeutic device that is portable and yet has capability to provide any one or a combination of different therapies.

Yet another object of the present disclosure is to provide a therapeutic device that enables therapy through external electrodes so as to apply therapy to areas that cannot be reached by hand.

Yet another object of the present disclosure is to provide a therapeutic device that allows ambidextrous application.

Still another object of the present disclosure is to provide a therapeutic device that incorporates wireless connectivity to enable uploading/downloading of therapeutic data as well as remote control of the device.

Various objects, features, aspects and advantages of the present invention will become more apparent from the detailed description of the invention herein below along with the accompanying drawing figures in which like numerals represent like components.

SUMMARY

Aspects of the present disclosure relate to a multifunctional device for providing therapy to human body. In an aspect, the disclosed multifunctional device incorporates means for any one or a combination of different therapies such as electric pulse therapy, U.V. therapy, Low energy laser therapy, and heat therapy to a human body part, thus making it a holistic therapeutic device.

In an aspect, the disclosed therapeutic device is a single device containing more than one kind of therapy systems that can be operated individually or simultaneously as per requirement. User can control & manage all therapy systems which are included in device using controls provided thereon.

In another aspect, the disclosed therapeutic device is double ended having a first end and a second end, wherein each end of the device incorporates capability to impart each of the above mentioned therapies either individually or in combination. In an aspect, one of the two ends say the first end, can be configured for providing therapy to a smaller area of human body, and the other end i.e. the second end, can be configured to provide therapy to a larger area of human body.

In an aspect, the disclosed device include slow energy photonic laser with a coupling system for each of the two sides (the first side also referred to as convergent side and the second side also referred to as divergent side). Each of the two sides can also have UV light emitters for UV therapy, electrodes for electric pulse therapy, heaters for heat therapy. In an aspect, the heaters for heat therapy can be placed behind the electrodes meant for electric pulse therapy. Thus, the electrodes are configured to provide both electric pulse therapy and the heat therapy.

The device can include a power supply, a molecular high voltage low amperage current intensity display and control system, and a low energy photonic laser coupling system for the convergent side and the divergent side. In an aspect, two separate low energy photonic laser systems can be provided in a single device in such a way that the systems can be used separately and independently of each other as per requirement. These two low energy photonic lasers with their coupling systems can be provided on opposite directions to each other.

In an embodiment, two low energy photonic lasers configured to provide low energy photonic laser treatment at two ends i.e. convergent side on the first end and divergent side on the second end, of the disclosed device can be identical, and difference in area covered by them is achieved by respective coupling system.

In an aspect, convergent side low energy photonic laser coupling system (or simply and interchangeably as "convergent side laser system" or "convergent laser system can be configured in a way that it results in focusing on a smaller output area due to convergence of low energy photonic laser output and can be used for therapy required at a smaller area. On the other hand, divergent side low energy photonic laser coupling system (or simply and interchangeably as "divergent side laser system" or "divergent laser system") can be arranged in a way that it results in focusing on larger output area due to divergence of the low energy photonic laser output and can therefore be used for therapy required at a larger area.

In another aspect, a display can be configured in the proposed device so as to display the intensity of molecular high voltage pulses, battery usage, mode of therapy and any other relevant information. In another aspect, the display can be configured to display the desired information on convergent side in front of operators while operating device from divergent side. In the same manner, the display can also show the desired data on divergent side in front of the operators while operating device from convergent side. In an aspect, intensity of the molecular high voltage low amperage current can be changed through encoder by operating a hand wheel engaged with the encoder through a gear. In an embodiment, the display can be any type as known in the related art such as but not limited to OLED display, capacitive touch display, or LED display In an aspect, display screen can automatically rotate as per usage of the operator and show the intensity of molecular high voltage low amperage current pulses as well as time for which low level low energy photonic laser has been operated. In another aspect, the display can be configured to enable a user to configure time for which the device is to be kept functional during one instance/operation, after which the device can automatically be switched off. The proposed display can therefore be used to preset a time for continuous operation till that much time before it gets off.

In another aspect, the proposed system can work on different principles firstly, on low level low energy photonic laser therapy (also simply and interchangeably referred to as "laser therapy" hereinafter) that supplies power to infrared low energy photonic laser diode from battery via circuit to enable low energy photonic laser rays to be emitted and passed from convergent or divergent side lenses separately as required. The laser rays penetrate the body and can be absorbed by cells to relief the pain. Secondly, micro molecular high voltage low amperage current electric stimulation (also simply and interchangeably referred to as "electric stimulation" hereinafter) having low voltage current supplied by a battery via circuit can be passed through the spaced apart electrodes (convergent side or divergent side separately as required) in the body, which promotes production of adenosine triphosphate (ATP) and protein that can repair cells and achieves pain relief. Thirdly, a current can be passed through heating elements/heaters positioned behind the electrodes to provide heat therapy. Fourthly, a set of UV emitters can be supplied with current to generate UV light to provide UV therapy.

In another aspect, on the convergent side, after supplying power from battery, low energy photonic laser emitted from the diode and low energy photonic laser rays passed through the concave lenses can be converged and focused at the smaller area. At the same time, electrodes used at the convergent side can be smaller for covering a smaller treating area. On divergent side, on the other hand, after supplying the power from battery, low energy photonic laser emitted from the diode and low energy photonic laser rays passed through the convex lenses can be diverged and focused at a larger area. At the same time, electrodes used at the divergent side can be larger for covering a larger treating area.

In an aspect, the disclosed device further includes wireless communication means such as but not limited to Bluetooth to enable transfer of therapy data to external devices such as a Laptop, a mobile phone, a tablet, a server etc. In addition, the communication means can also be used for remotely controlling the device function if required.

Yet another aspect discloses a single device for switching power for low energy photonic laser output and electrode supply on dual sides one by one covering smaller area and larger area for making treatment more convenient and better.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms as used herein are shown below. To the extent a term used in a claim is not defined below, it should be given the broadest definition persons in the pertinent art have given that term as reflected in printed publications and issued patents at the time of filing.

Aspects of the present disclosure relate to a multifunctional device for providing healing therapy to human body. As known in the related art, different kinds of therapies are used for different purposes. For example, U.V Lights are used for skin disorders including atopic skin disorder. Electric pulse stimulation is used or applied to adherent human myotubes and for pain relief & muscle toning. Low energy lasers are used for treatment of various tissue injuries and heat is used for pain relief of muscles.

Figure 1A:
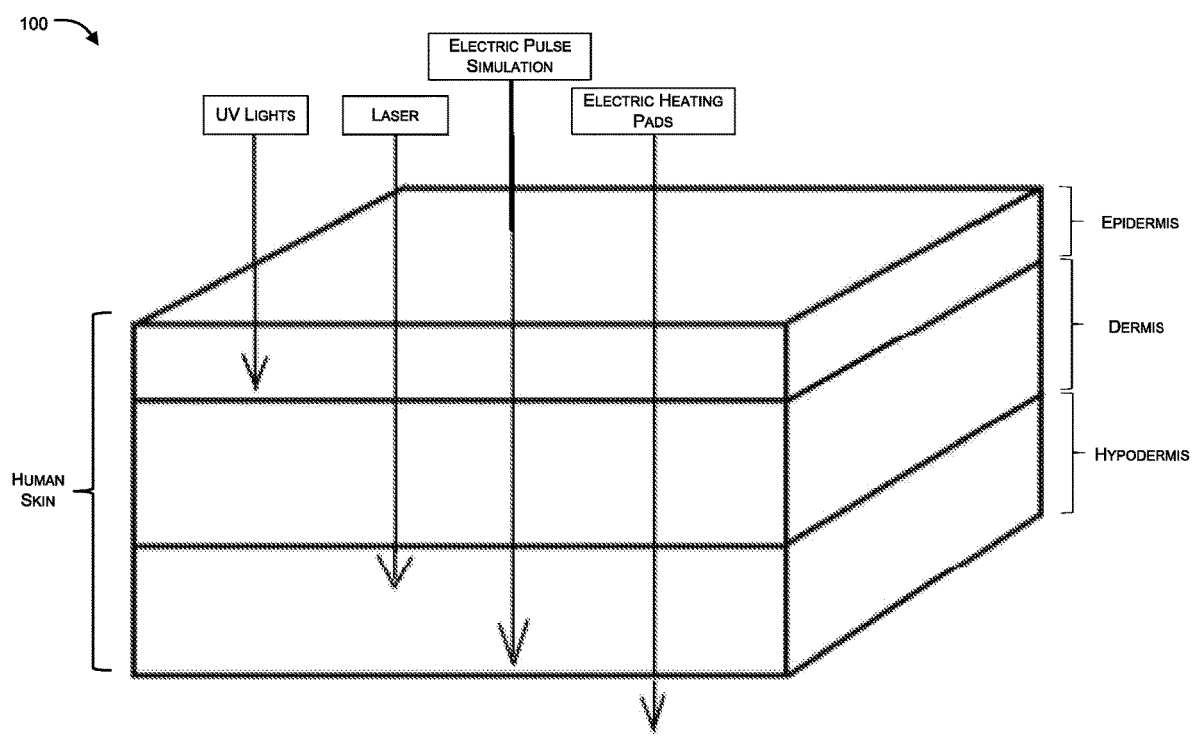
FIG. 1A illustrates an exemplary representation of penetration of various healing methods typically used in the related art.

FIG. 1A illustrates an exemplary representation of penetration of various healing methods typically used in the related art. UV Light can penetrate human skin depending on its strength/power up to a depth of 40 microns to 400 microns. Laser can penetrate up to 30 mm depth. Electric pulse stimulation penetrates around 40 to 50 mm and electric heating pads penetrate up to 2-inch depth in body. Thus, any therapy device that is based on any one of above therapy shall limit the effective range to corresponding value only restricting the scope of their use. Accordingly, depending on need a corresponding therapy device needs to be provided. Therefore, multiple devices have to be kept to meet varying requirements. In an aspect, the disclosed device incorporates all the four therapies i.e. Laser, Electric heaters, Electric pulse stimulation and UV Lights, so that a user can operate or use any one or a combination of more than one therapies at any one time for healing thus providing an holistic treatment.

In an aspect, the disclosed therapeutic device is a single device containing more than one kind of therapy systems that can be operated individually or simultaneously as per requirement. User can control & manage all therapy systems which are included in device using controls provided thereon.

In another aspect, the disclosed therapeutic device is double ended wherein each end of the device incorporates capability to impart each of the above mentioned therapies either individually or in combination. In an aspect, one of the two ends can be configured for providing therapy to a smaller area of human body, and the other end can be configured to provide therapy to a larger area of human body.

In an aspect, the disclosed device includes low energy photonic laser with a coupling system for each of the two sides (referred to as first side or convergent side, and second side or divergent side and these terms have been used interchangeably). Each of the two sides can also have UV light emitters for UV therapy, electrodes for electric pulse therapy, heaters for heat therapy. In an aspect, the heaters for heat therapy can be placed behind the electrodes meant for electric pulse therapy. Thus, the electrodes are configured to provide both electric pulse therapy and the heat therapy.

The device can include a power supply, a molecular high voltage low amperage current intensity display and control system, and a low energy photonic laser coupling system for the convergent side and the divergent side. In an aspect, two separate low energy photonic laser systems can be provided in a single device in such a way that the systems can be used separately and independently of each other as per requirement. These two low energy photonic lasers with their coupling systems can be provided on opposite directions to each other.

In an embodiment, two low energy photonic lasers configured to provide low energy photonic laser treatment at two ends i.e. convergent side and divergent side, of the disclosed device can be identical, and difference in area covered by them is achieved by respective coupling system.

In an aspect, convergent side low energy photonic laser coupling system (or simply and interchangeably as "convergent side laser system" or "convergent laser system can be configured in a way that it results in focusing on a smaller output area due to convergence of low energy photonic laser output and can be used for therapy required at a smaller area. On the other hand, divergent side low energy photonic laser coupling system (or simply and interchangeably as "divergent side laser system" or "divergent laser system") can be arranged in a way that it results in focusing on larger output area due to divergence of the low energy photonic laser output and can therefore be used for therapy required at a larger area.

In another aspect, a display can be configured in the proposed device so as to display the intensity of molecular high voltage pulses, battery usage, mode of therapy and any other relevant information. In another aspect, the display can be configured to display the desired information on convergent side in front of operators while operating device from divergent side. In the same manner, the display can also show the desired data on divergent side in front of the operators while operating device from convergent side. In an aspect, intensity of the molecular high voltage low amperage current can be changed through encoder by operating a hand wheel engaged with the encoder through a gear. In an embodiment, the display can be any type as known in the related art such as but not limited to OLED display, capacitive touch display, or LED display In an aspect, display on the display screen can automatically rotate as per usage of the device and show the intensity of molecular high voltage low amperage current pulses as well as time for which low level low energy photonic laser has been operated. In another aspect, the display can be configured to enable a user to configure time for which the device is to be kept functional during one instance/operation, after which the device can automatically be switched off. The proposed display can therefore be used to preset a time for continuous operation till that much time before it gets off.

In another aspect, the proposed system can work on different principles firstly, on lowlevel low energy photonic laser therapy (also simply and interchangeably referred to as "laser therapy" hereinafter) that supplies power to infrared low energy photonic laser diode from battery via circuit to enable low energy photonic laser rays to be emitted and passed from convergent or divergent side lenses separately as required. The laser rays penetrate the body and can be absorbed by cells to relief the pain. Secondly, micro molecular high voltage low amperage current electric stimulation (also simply and interchangeably referred to as "electric stimulation" hereinafter) having low voltage current supplied by a battery via circuit can be passed through the spaced apart electrodes (convergent side or divergent side separately as required) in the body, which promotes production of adenosine triphosphate (ATP) and protein that can repair cells and achieves pain relief. Thirdly, a current can be passed through heating elements/heaters positioned behind the electrodes to provide heat therapy. Fourthly, a set of UV emitters can be supplied with current to generate UV light to provide UV therapy.

In another aspect, on the convergent side, after supplying power from battery, low energy photonic laser emitted from the diode and low energy photonic laser rays passed through the concave lenses can be converged and focused at the smaller area. At the same time, electrodes used at the convergent side can be smaller for covering a smaller treating area. On divergent side, on the other hand, after supplying the power from battery, low energy photonic laser emitted from the diode and low energy photonic laser rays passed through the convex lenses can be diverged and focused at a larger area. At the same time, electrodes used at the divergent side can be larger for covering a larger treating area.

Yet another aspect discloses a single device for switching power for low energy photonic laser output and electrode supply on dual sides one by one covering smaller area and larger area for making treatment more convenient and better.

Figure 1B:
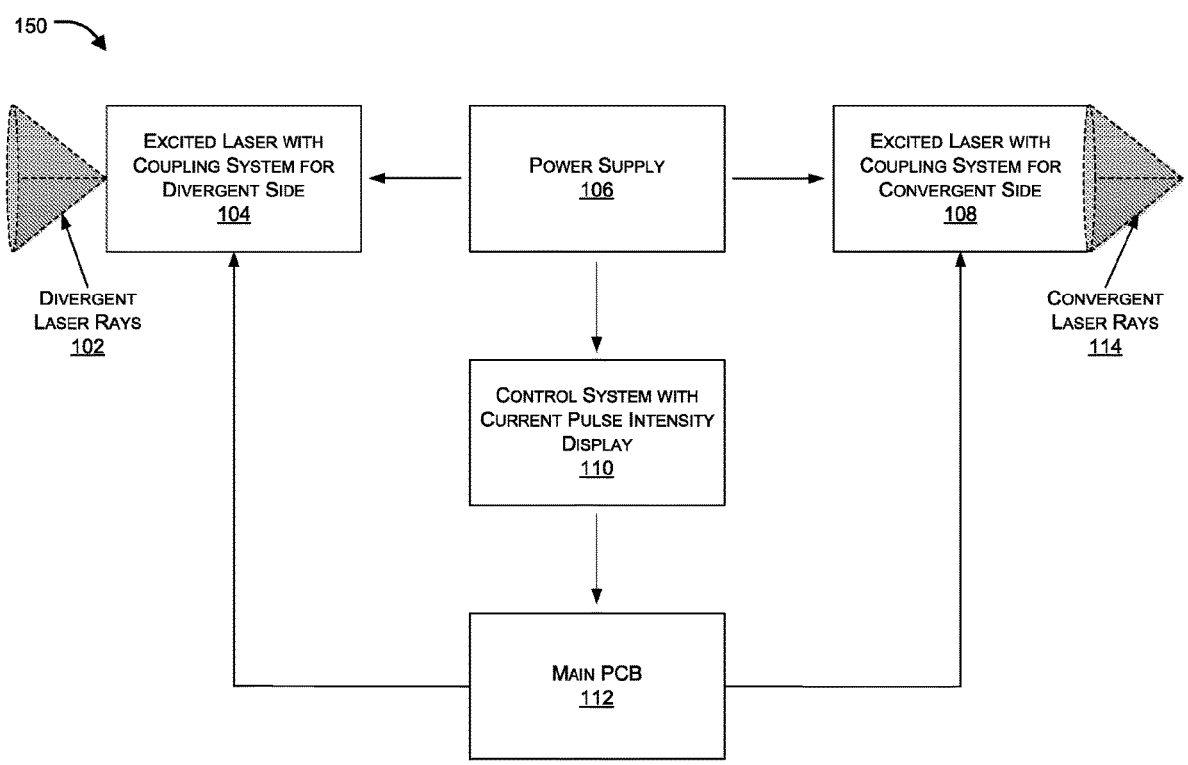
FIG. 1B illustrates a block diagram of proposed system for multifunctional low energy photonic laser treatment in accordance with embodiments of the present disclosure.

FIG. 1B illustrates an exemplary block diagram of the proposed system for multifunctional low energy photonic laser treatment in accordance with an embodiment of the present disclosure. As shown in the block diagram 100, the proposed system can include a power supply 106, a molecular high voltage low amperage current intensity display and control system 110, an excited laser with coupling system for convergent side 108 emitting convergent laser rays 114, and excited laser with coupling system for divergent side 104 emitting divergent laser rays 102. All the components of the system can be integrated and connected together via main PCB 112. In an aspect, two separate low energy photonic laser systems can be provided in a single device in such a way that the systems can be used separately and independently of each other as per requirement. These two low energy photonic lasers with their coupling systems can be provided on opposite directions to each other.

In an embodiment, two low energy photonic lasers configured to provide low energy photonic laser treatment at two ends of the disclosed device can be identical, and difference in area covered by them is achieved by arranging divergent lens system (for larger end) and convergent lens system (for smaller end). Accordingly, the two sides are being respectively called as convergent side low energy photonic laser system 108 and divergent side low energy photonic laser system 104 (also referred to as first end and second end respectively), wherein the convergent side system 108 can be arranged in a way that results in focusing on smaller area due to convergence of low energy photonic laser output and can be used for therapy required at a smaller area. On the other hand, divergent side system 104 can be arranged in a way that results in focusing on larger area due to divergence of the low energy photonic laser output and can be used for therapy required at a larger area.

In an embodiment, means for other therapies i.e. Electric heaters, Electric pulse stimulation and UV Lights can also be configured at each of the two ends in corresponding sizes and locations to enable any one or combination of the therapies from the either end.

In another embodiment, the proposed system can include a single display panel such as but not limited to a LED display panel, with controls that can enable presentation of intensity of therapy, mode of therapy and battery usage and any other useful information. In particular, it can display molecular high voltage low amperage current pulses in respect of laser treatment as also corresponding parameters for other therapies on the convergent side in front of operators while operating the device from divergent side. Similarly, the display panel can show the intensity of molecular high voltage low amperage current pulses in respect of the laser treatment as also corresponding parameters for other therapies on the divergent side in front of the operators while operating the device from convergent side. The display on the screen of the single display panel can automatically rotate the displayed information as per usage of the operator, and can show the treatment parameters as well as, for instance, time for which treatment has been imparted.

In another embodiment, the proposed system can include a low-level low energy photonic laser therapy (also simply referred to as "laser therapy") that supplies power to infrared low energy photonic laser diode (also referred to as "photonic laser diode" or simply as "diode") from the power supply 106 via the main PCB circuit 112. Low energy photonic laser rays emitted can be passed from convergent or divergent side lenses separately as required, wherein the laser rays penetrate body and can be absorbed by cells to relief pain. The proposed system can further include a micro-molecular high voltage low amperage current electric stimulation (also simply referred to as electric simulation) having low voltage current being supplied by battery 106 via circuit 112 and being passed through spaced apart electrodes (convergent side or divergent side separately as required) in the body, which promotes production of adenosine triphosphate (ATP) and protein that can repair cells and achieve pain relief. Also, the intensity of molecular high voltage low amperage current can be changed through an encoder by operating a hand wheel that is engaged with the encoder by means of a gear.

In another exemplary embodiment, on the convergent side 108, after supplying power from battery 106, low energy photonic laser emitted from the diode and low energy photonic laser rays 114 passed through concave lenses can be converged and focused at a smaller area. At the same time, electrodes used at the convergent side 108 can be smaller for covering a smaller treating area. On divergent side 104, after supplying power from battery 106, low energy photonic laser emitted from the diode and low energy photonic laser rays 102 passed through convex lenses can be diverged and focused at a larger area. At the same time, electrodes used at the divergent side 104 can be larger for covering a larger treating area.

Figure 2:
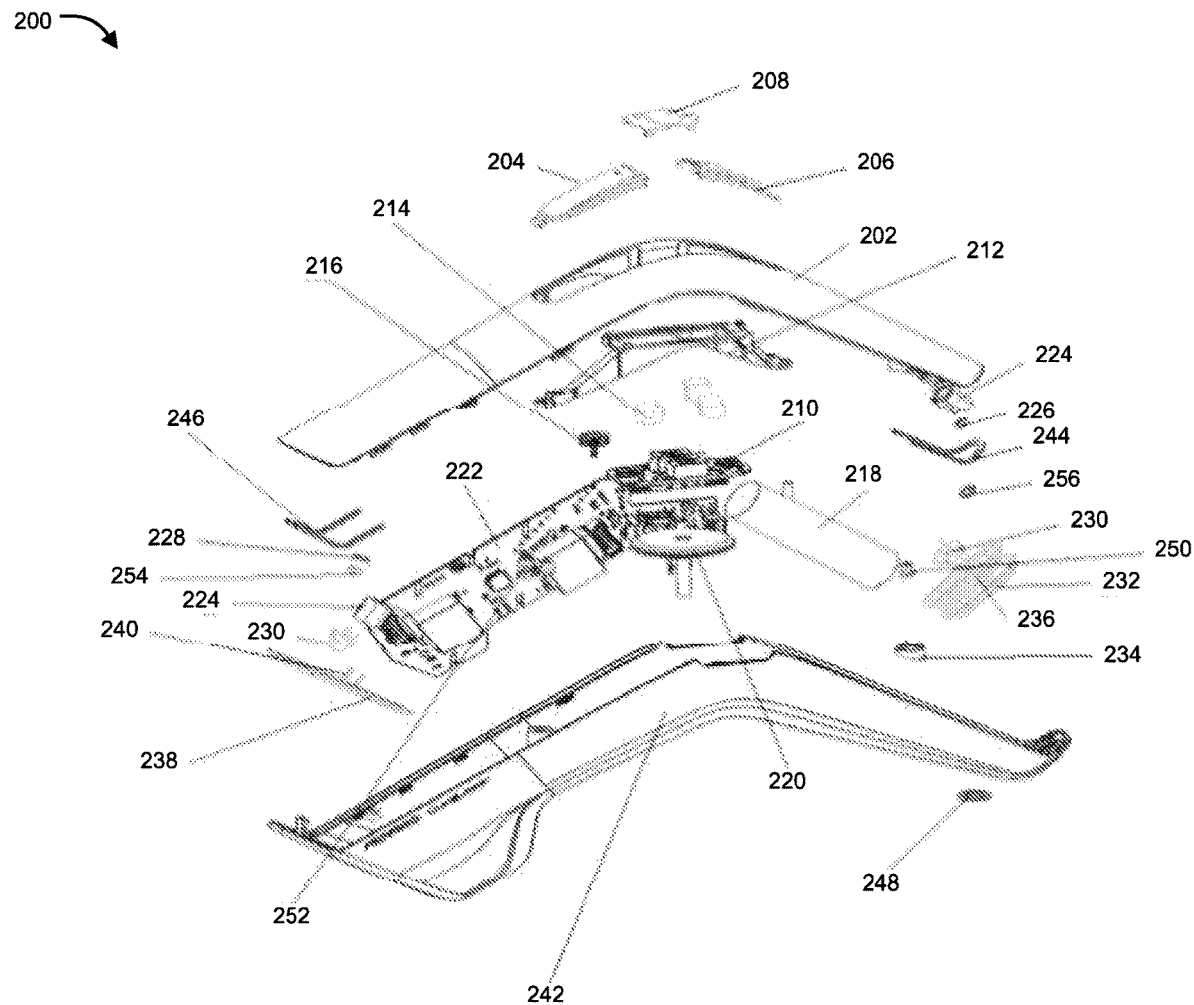
FIG. 2 illustrates an exemplary exploded view of low energy photonic laser device in accordance with embodiments of the present disclosure.

FIG. 2 illustrates an exemplary exploded view of the proposed low energy photonic laser device in accordance with an embodiment of the present disclosure. The device 200 in exploded view shows a top cover 202 containing a fine switch 204 fitted by means of screws to activate convergent side low energy photonic laser, a large switch 206 fitted by means of screws to activate divergent side low energy photonic laser, and a display cover 208 made from say transparent plastic material.

In an aspect, molecular high voltage low amperage current pulses intensity can be set as per requirement and the corresponding value can be seen through the display cover 208. Snaps and snap grooves can be provided in the top cover 202 for attaching top cover. In another aspect, add-on PCB brackets 212 can be mounted on top cover 202 through clamping boss 202d and have snaps for clamping the add-on PCB 210, and contains convergent side as well as divergent side operating switch.

In an aspect, light guide 214 and encoder gear 216 can be driven by a hand wheel gear, which can further include an integral hexagonal shaft that can be fitted inside of the encoder present on main PCB 222. Battery as power source 218 can be used for supplying power to the circuits, wherein the hand wheel 220 can be a manually operated hand wheel made from plastic material and can be used for changing voltage of the given power supply. In an aspect, the hand wheel 220 can further be used as a selection tool for individual or combined types of therapy. It can further be configured to preset a time after, for instance, along press of ON-OFF button for convergent and divergent sides respectively.

In an embodiment, a hand wheel gear can be attached with the hand wheel 220 for rotating the encoder gear 216. A circular shaft can be an integral part of the hand wheel 220, and can be fitted and located inside of hollow boss. In an aspect, the circular shaft can rotate on its own axis, wherein a hand wheel locator and guiding slots can be provided in the hand wheel 220 for guiding of the hand wheel 220 on a hand wheel locating or guiding boss that is configured at bottom cover 242.

In another exemplary embodiment, the main PCB 222 can include a USB charging port for charging power source battery 218, a connector for connecting USB charging port to the battery power source 218, a transformer to change voltage as per requirement for operating encoder through hand wheel 220. In an exemplary implementation, the transformer can change voltage of the provided power supply for convergent and divergent side electrodes by means of respective convergent side and divergent side power supply connector. In another aspect, encoder present in the main PCB 222 can include an encoder that can be used to change molecular high voltage low amperage current flow as per requirement. The encoder can be operated through an encoder gear 216 and hand wheel 220. On rotation of the hand wheel 220, the encoder can rotate by changing molecular high voltage low amperage current that passes to the electrodes, wherein the magnitude of voltage can be set as per requirement.

In another embodiment, convergent side (low energy photonic) laser holder 224 can locate and hold a laser source such as a low energy photonic laser diode 230, springs 236, convergent side lens 1226, and convergent side lens 2 256. Similarly, divergent side low energy photonic laser holder can locate and hold low energy photonic laser diode 230, springs 240, divergent lens 1228 and divergent side lens 2 254.

In another embodiment, laser diode 230 can be connected to the power supplying battery 218, and can emit low energy photonic laser rays when excited. Diode 230 can befitted and located inside of the divergent side low energy photonic laser diode holder 224.

In another embodiment, convergent side electrode 232 made of titanium alloy, for instance, can be fitted and located at convergent side electrode mounting face in a bottom cover 242 that can be smaller than the divergent side electrode for covering a smaller area for treatment. Divergent side electrode 238 made of titanium alloy, for instance, can be fitted and located at divergent side electrode mounting face in bottom cover 242 that can be larger than the convergent side electrode for covering a larger area for treatment.

In another embodiment, screw cover 234 covers the opening of the clamping screw 250 for bracket. Bottom cover 242 can include snaps as an integral part for clamping that can be fitted with top cover snap, hand wheel locating boss for accurately locating and guiding hand wheel 220 on being matched with hand wheel's locator and guiding slot. Hand wheel opening slot can be provided in the bottom cover for opening hand wheel 220, a hollow boss for locating or holding a hand wheel shaft and for mounting of bottom cover clamping screw in bottom cover clamping boss clamped in screw clamping boss. Bottom cover 242 further includes a convergent side electrode mounting face for making convergent side electrode 232 rest on the face, an opening cut out for screw cover of the bottom cover clamping screw, an opening cut out provided in the bottom cover 242 for USB charging port, and a divergent side electrode 238 that rests on the divergent side electrode mounting face.

In another embodiment, convergent side EVA 244 and divergent side EVA 246 can be placed between the top cover 202 and the bottom cover 242, which can act as a sealing and prevent any gel used during therapies from coming inside the body. Suitable screws can be used to seal the convergent and divergent side EVAs with the body, wherein main body screw 250, a threaded insert, can befitted in the top cover 202 for joining whole outer body of the device.

Figure 3:
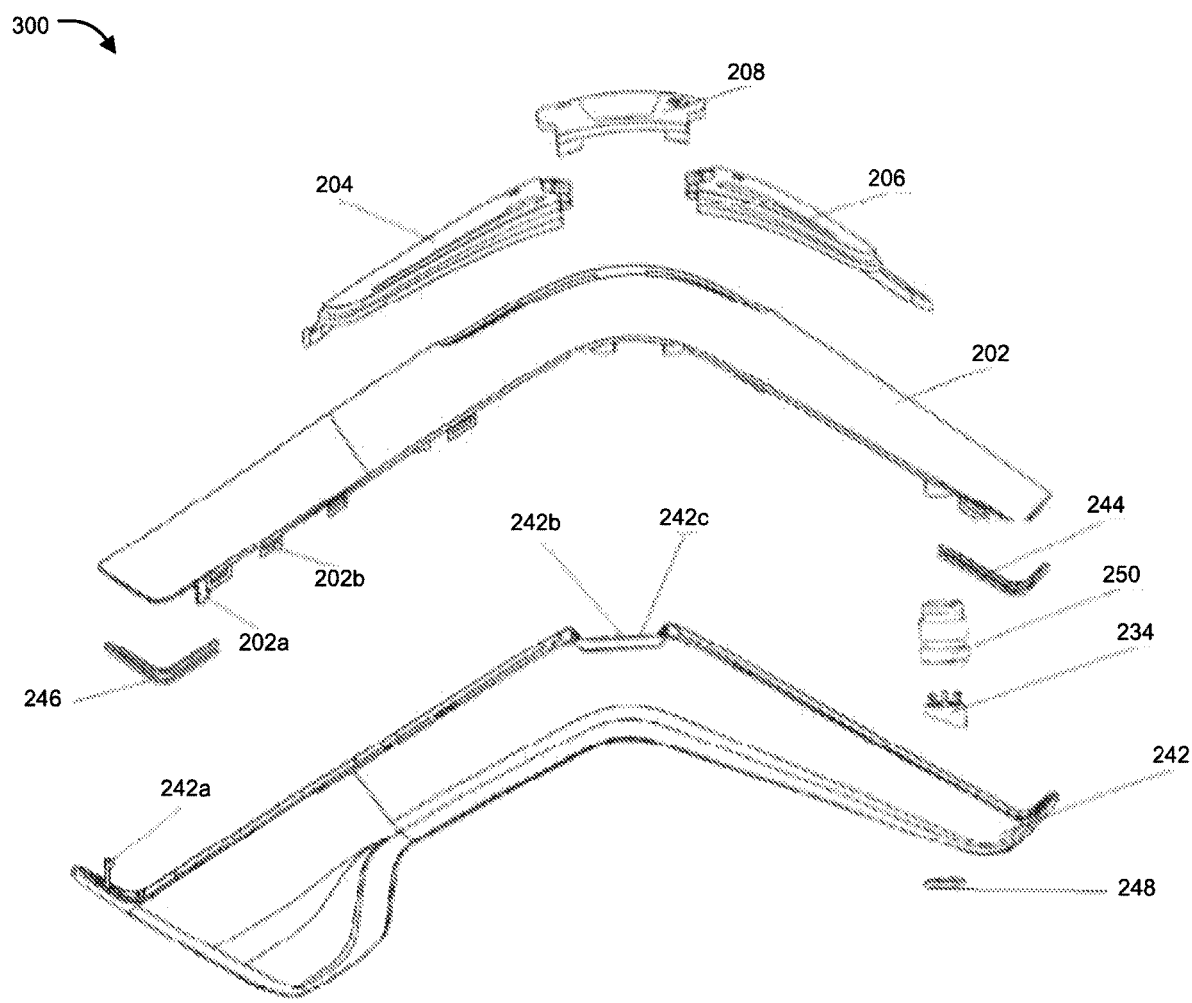
FIG. 3 illustrates main outer body configuration of the proposed device in accordance with embodiments of the present disclosure.

FIG. 3 illustrates an exemplary representation of the main outer body configuration of the proposed device 200 in accordance with an embodiment of the present disclosure. The configuration 300 shows a top cover 202 that includes a fine switch 204 used for activating the convergent side low energy photonic laser, large switch 206 used for activating divergent side low energy photonic laser, and a display cover 208 made from transparent plastic material that can present and enable setting/change of the current pulses intensity as per requirement. The value can be shown in digital form through a transparent cover. In an aspect, snaps 202a, and snaps grooves 202b can be provided in the top cover 202 for fitting the bottom cover 242. Convergent side EVA 244 and divergent side EVA 246 can be placed between the top cover 202 and the bottom cover 242 that prevents gel from coming inside the body of device by acting as a sealing.

Figure 4A:
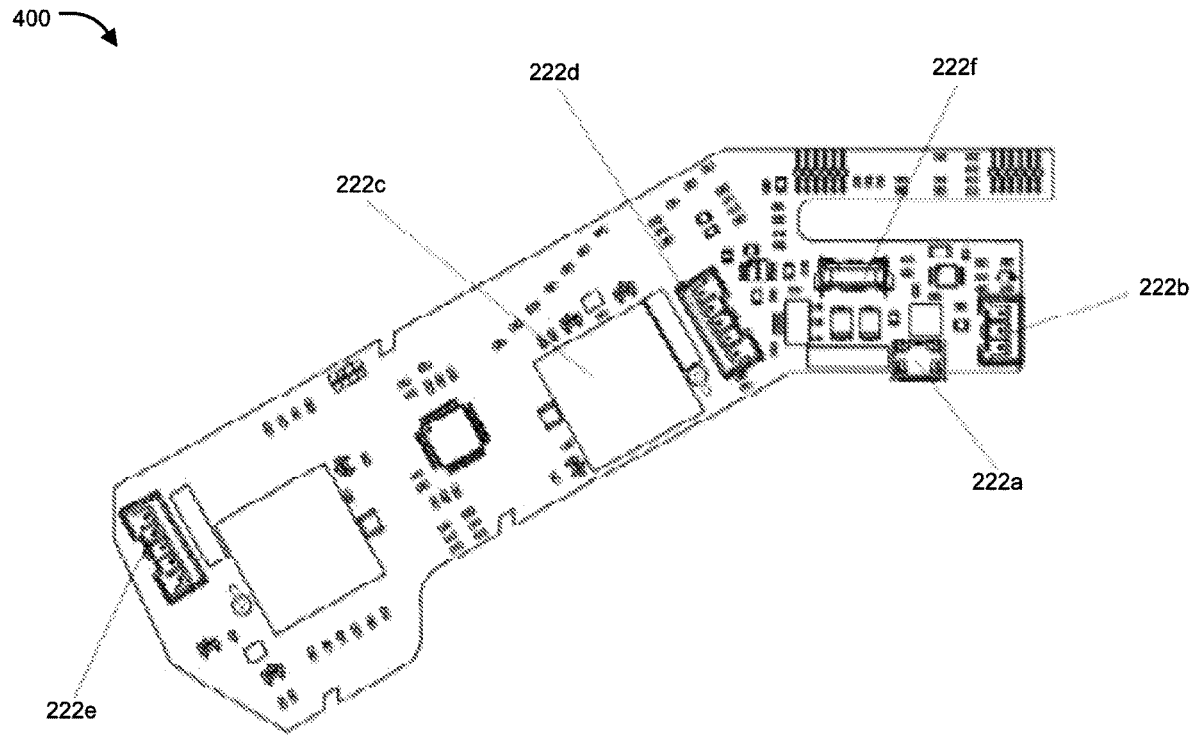
FIG. 4A illustrates main PCB in accordance with an embodiment of the present disclosure.

FIG. 4A illustrates an exemplary main PCB of the disclosed device 200 in accordance with an embodiment of the present disclosure. As shown in the exemplary configuration 400, main PCB 222 can include a USB charging slot 222a for charging battery, a connector 222b for battery to befitted for connecting the battery to the circuit(s), an encoder 222f that can be used for changing current pulses intensity as per requirement at the electrodes end and can be operated via an encoder gear 216 through a hand wheel 220. Convergent side power supply connector 222d can be fixed in the main PCB 222 for supplying power to the convergent side electrode and low energy photonic laser emitting diode. Divergent side power supply connector 222e can be fixed in the main PCB 222 for supplying power to divergent side electrode and low energy photonic laser emitting diode.

In an aspect, the disclosed device 200 can also include wireless communication means such as but not limited to Bluetooth to enable transfer of therapy data to external devices such as a Laptop, a mobile phone, a server etc. In addition, the communication means can also be used for and remotely controlling the device function if required. For this, there can be a wireless communication module. Alternatively, means for communication may be configured within the microcontroller 222c.

Figure 4B:
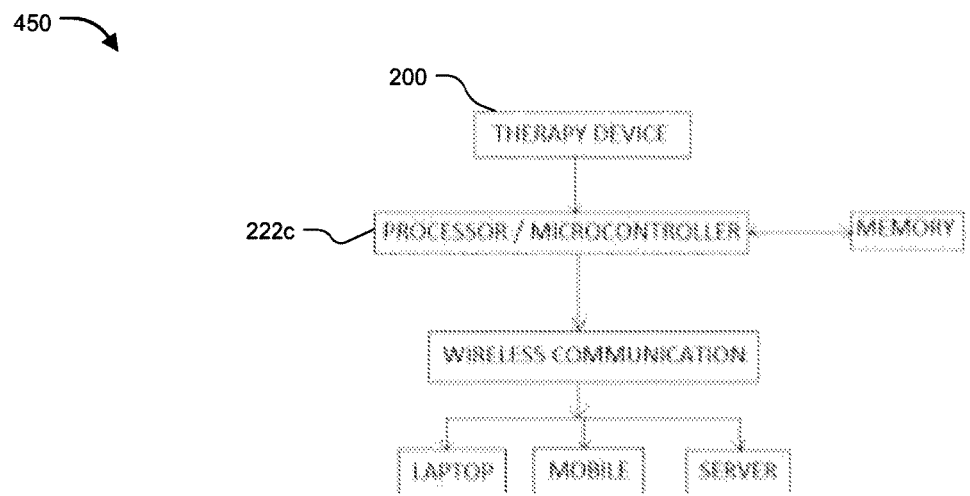
FIG. 4B illustrates an exemplary block diagram of process control and wireless communication system in the disclosed therapy device in accordance with embodiments of the present disclosure.

FIG. 4B illustrates an exemplary block diagram 450 of therapy device process control and wireless communication.

As shown in the block diagram 450 functional components can include a processor or microcontroller 222c for controlling and monitoring process of healing, memory for storing & recording therapy process data. In addition there can be wireless communication means can be either provided separately or integrated within the microcontroller 222c for transferring data to external devices such as but not limited to a Laptop, a mobile, server or any other medical device for analysis of the treatment. Same way the wireless communication can be used for uploading data from any external communication platforms to the disclosed device 200 for security, safety, upgrade of firmware, and remotely controlling the device function. Wireless communication module can work based on any of the known technologies such as but not limited to Bluetooth, Wi-Fi to name a few.

Figure 5:
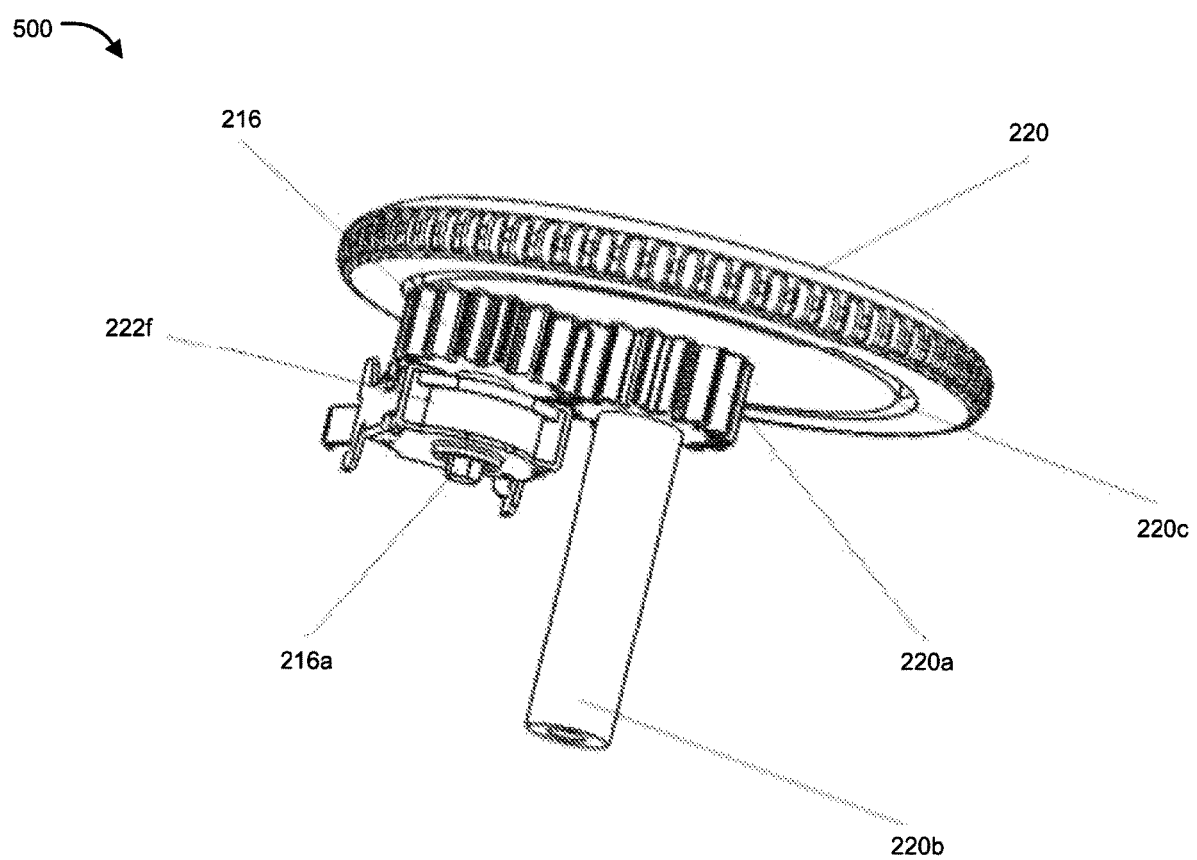
FIG. 5 illustrates an encoder and gear assembly in accordance with an embodiment of the present disclosure.

FIG. 5 illustrates an encoder and gear assembly of the disclosed device 200 in accordance with embodiments of the present disclosure. As shown in assembly 500, hand wheel 220 that is free to rotate by 360 degrees, can be configured in a circular round shape for easy holding and revolving to enable change in intensity of the current pulses as desired. Hand wheel gear 220a can be attached with the hand wheel 220 for rotating encoder gear 216. Circular shaft for hand wheel 220a can be attached as an integral part of the hand wheel 220 that can be fitted in the bottom cover 242d and can rotate freely on its axis. Encoder gear 216 can be driven by a hand wheel gear 220, and a hexagonal shaft 216a that is made as an integral part of the encoder gear 216 can be fitted inside of the encoder hole of encoder 222f fitted with the PCB.

Figure 6:
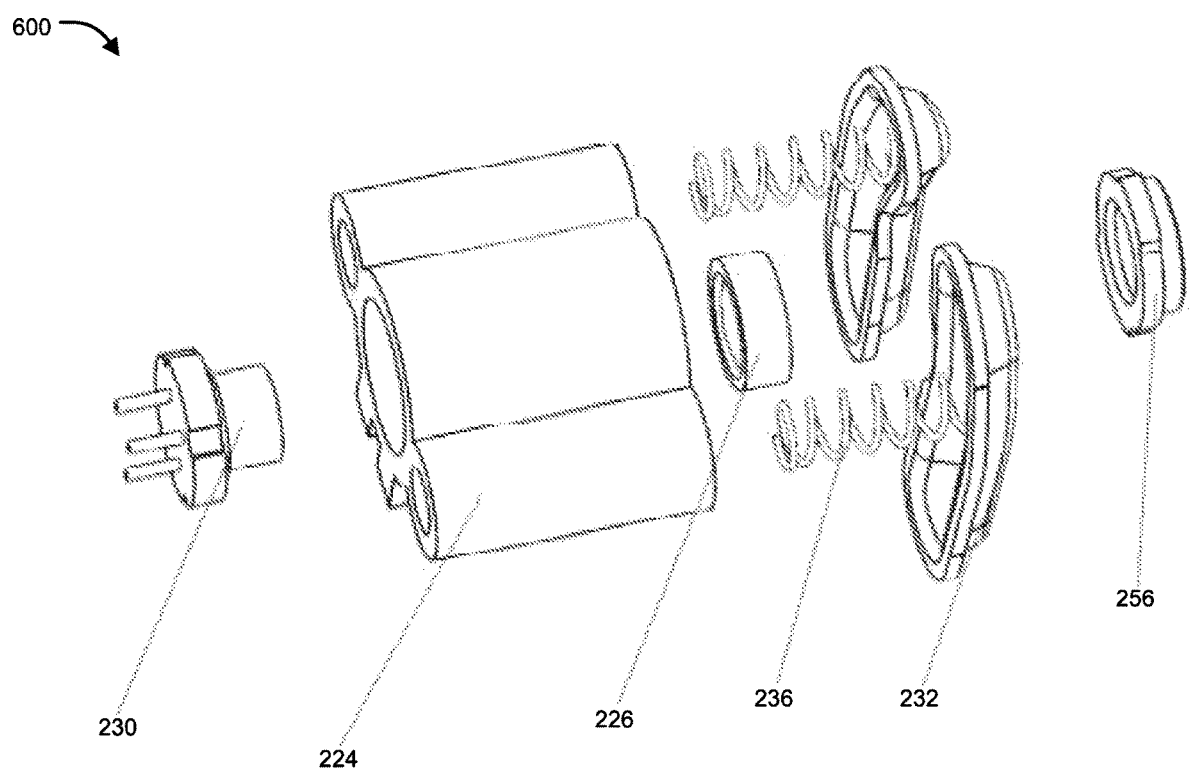
FIG. 6 illustrates convergent side laser emitting and coupling system in accordance with an embodiment of the present disclosure.

FIG. 6 illustrates convergent side low energy photonic laser emitting and coupling system in accordance with embodiments of the present disclosure. As shown in FIG. 600, convergent side low energy photonic laser coupling and emitting system can include convergent side electrodes 232 made of, for instance, titanium alloy that can be fitted and located at convergent side electrode mounting face 242g in bottom cover 242. Convergent side low energy photonic laser diode holder 224 can locate and hold the convergent lens 1 226 and lens 2 256 at appropriate positions in the system at bottom side of the low energy photonic laser diode holder 224. Convergent side springs 236 located and held in the convergent side low energy photonic laser diode holder 224 can be connected to the convergent side electrodes 232 so as to continuously remain in contact with the convergent side electrodes 232 from one side and to the power supplying battery for supplying power to the electrodes from other side. A laser source such as an infrared low energy photonic laser diode 230 can be placed inside the convergent side low energy photonic laser diode holder 224 from top portion. Low energy photonic laser diode holder 224 can maintain continuous contact with the power supply and PCB.

In an aspect, two laser sources and respective holders, i.e. low energy photonic laser diode holder 224 and inferred low energy photonic laser diode 230, located on convergent side and divergent side respectively can be identical thereby reducing variety and improving maintainability.

Figure 7:
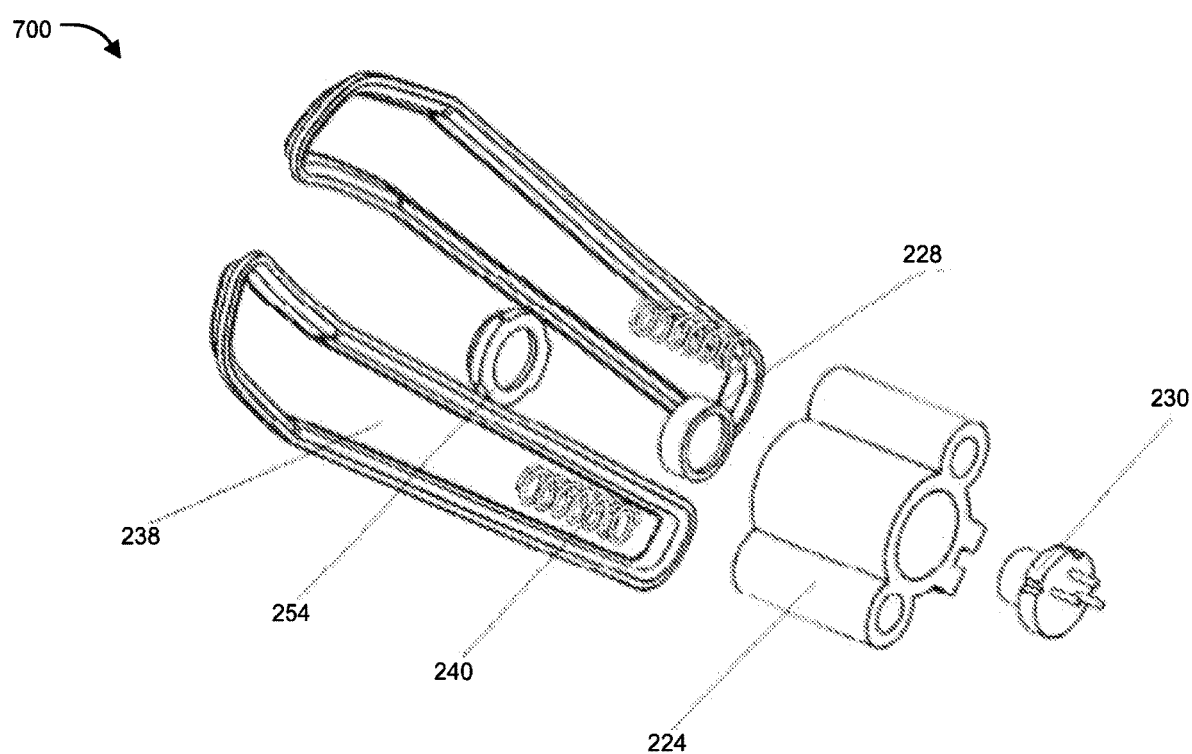
FIG. 7 illustrates divergent side laser emitting and coupling system in accordance with an embodiment of the present disclosure.

FIG. 7 illustrates divergent side low energy photonic laser emitting and coupling system in accordance with embodiments of the present disclosure. As shown in diagram 700, a divergent side low energy photonic laser coupling and emitting system can include divergent side electrodes 238 made of, for instance, titanium alloy fitted and located at divergent side electrode mounting face 242l in bottom cover 242. Divergent side low energy photonic laser diode holder 224 can locate and hold divergent lens 1 228 and lens 2 254 at appropriate positions in the system at bottom side of the low energy photonic laser diode holder 224. Divergent side springs 240 can be located and held in divergent side low energy photonic laser diode holder 224 connected to divergent side electrodes 238 that continuously remain in contact with the electrodes 238 from one side and to power supply battery from other side supplying power to the electrode. Laser source i.e. Diode 230 can be located and placed inside of the divergent side low energy photonic laser diode holder 224 from top portion of the low energy photonic laser diode holder. Low energy photonic laser diode holder can maintain a continuous contact with the power supply and PCB.

Figure 8:
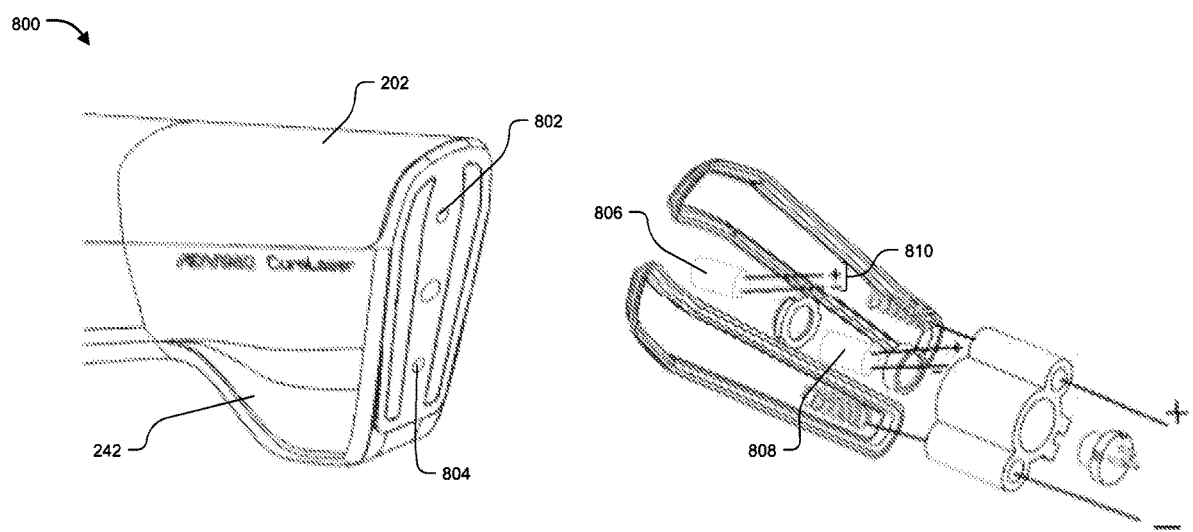
FIG. 8 illustrates an exemplary exploded view showing integration of ultraviolet light with main body.in accordance with embodiments of the present disclosure

FIG. 8 illustrates an exemplary exploded view showing ultraviolet light configured with main body in accordance with embodiments of the present disclosure. Ultraviolet light system 800 can include UV light 01 806, UV Light 02 808, UV Light holder 01 802 and UV Light holder 02 804. UV Light holder 01 802 and UV Light holder 02 804 are integrated with bottom cover 242 for accommodating UV light 01 806 and UV Light 02 808 respectively. UV light 01 806 and UV Light 02 808 are connected with PCB for getting control and power for operation. When a user operates the switch for starting therapy, U.V lights get the power from power source 218 through PCB 222, generating UV Lights, which are transferred on human skin for healing.

Figure 9:
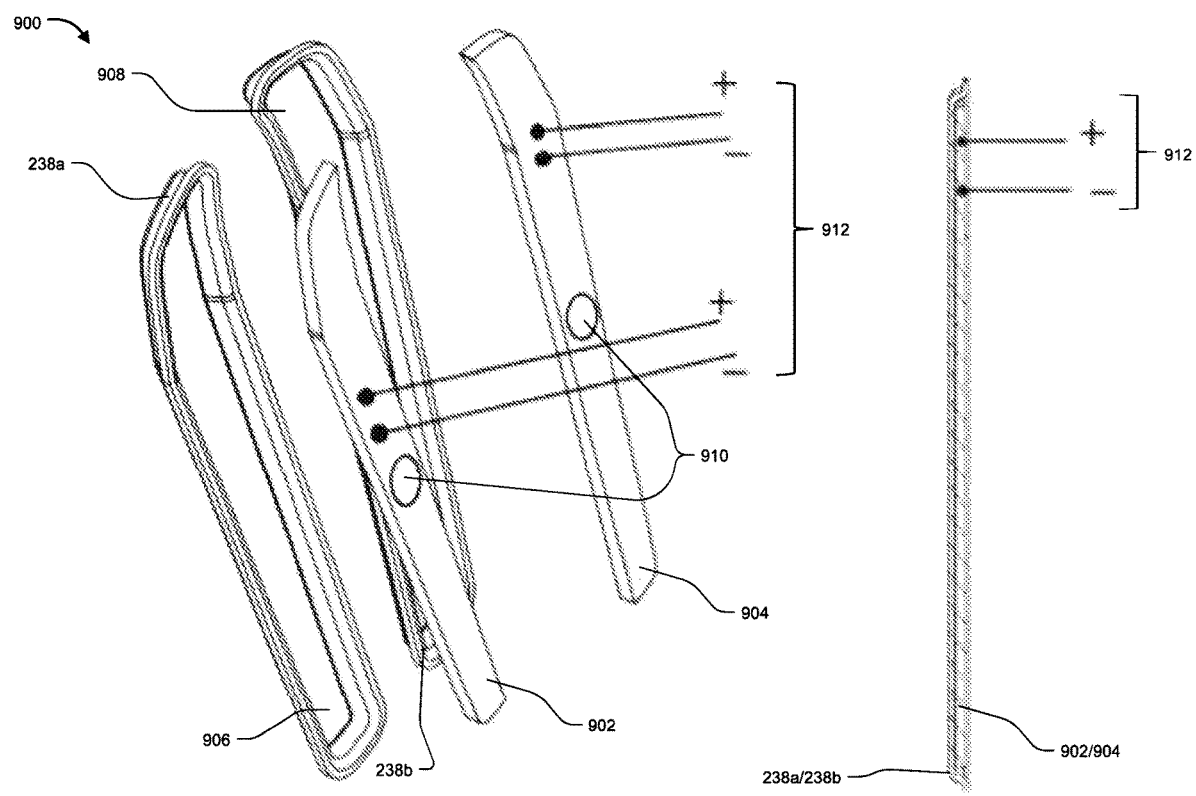
FIG. 9 illustrates an exemplary exploded view showing integration of electric heaters with electrodes in accordance with embodiments of the present disclosure.

FIG. 9 illustrates an exemplary exploded view showing arrangement of electric heaters with electrodes in accordance with embodiments of the present disclosure. Electric heaters healing system 900 can include left side heater 902, right side heater 904 and divergent side electrode 238. Both the heaters can have cut outs 910 for providing space to divergent side spring 240. Left side heater 902 can be fixed with left side electrode internal face 906 and right side heater 904 can be fixed with right side electrode internal face 908. Left side heater 902 and right side heaters 904 can be connected with PCB 222 through power supply connecting wires for getting power supply.

Figure 10:
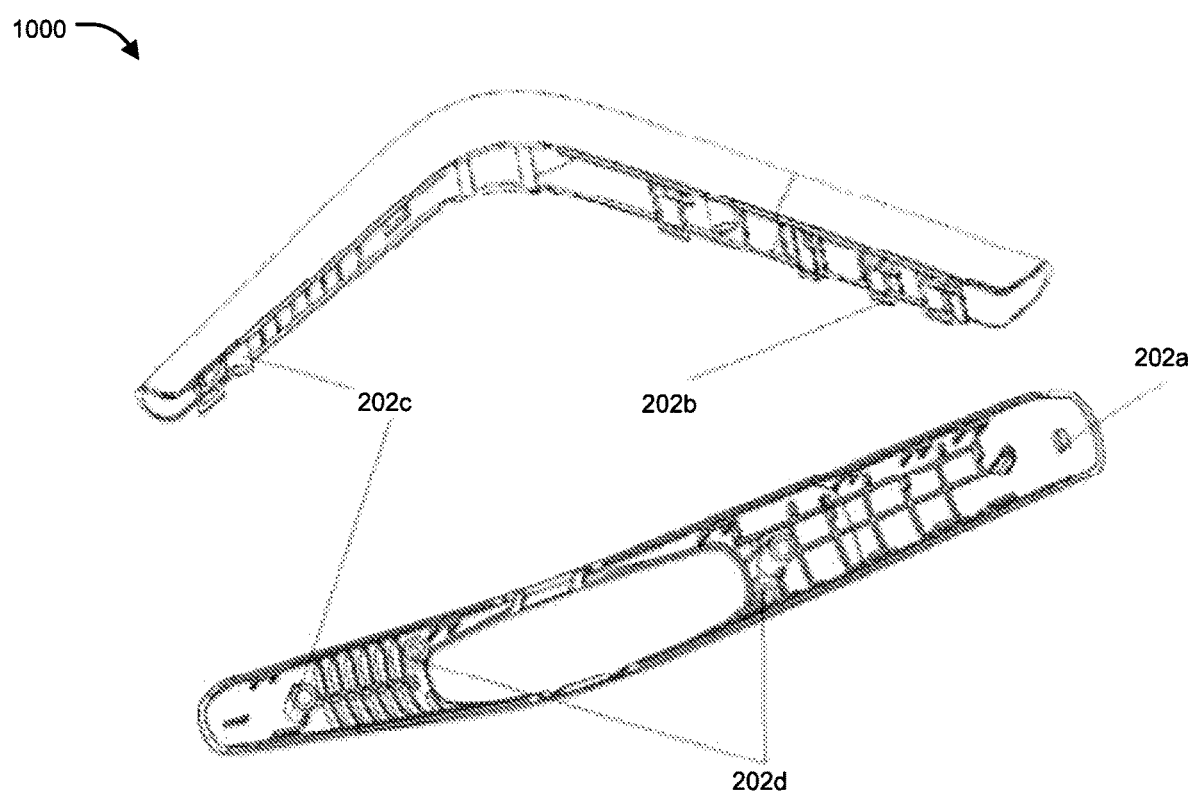
FIG. 10 illustrates top cover of the proposed device in accordance with an embodiment of the present disclosure.

FIG. 10 illustrates top cover of device 200 in accordance with embodiments of the present disclosure. As shown in diagram 1000, snaps 202a, snap grooves 202b, screw clamping boss 202c, and 202d can be provided in top cover 202. Snaps 202a can be an integral part of the top cover 202 used for clamping purpose. Snaps 202a can be fitted with the bottom cover snap 242a. Snap grooves 202b can be used for clamping purpose. Snap grooves 202b can be fitted with the bottom cover snaps 242o. Screw clamping boss 202c can receive a metal insertion. Screw clamping boss 202c can be provided for clamping bottom cover with the use of bottom cover clamping screw 242e. Screw clamping boss 202d can receive a metal insertion. Screw clamping boss 202d can be provided for clamping an add-on PCB bracket 212. In addition, bracket screw 252 can be inserted in the boss.

Figure 11:
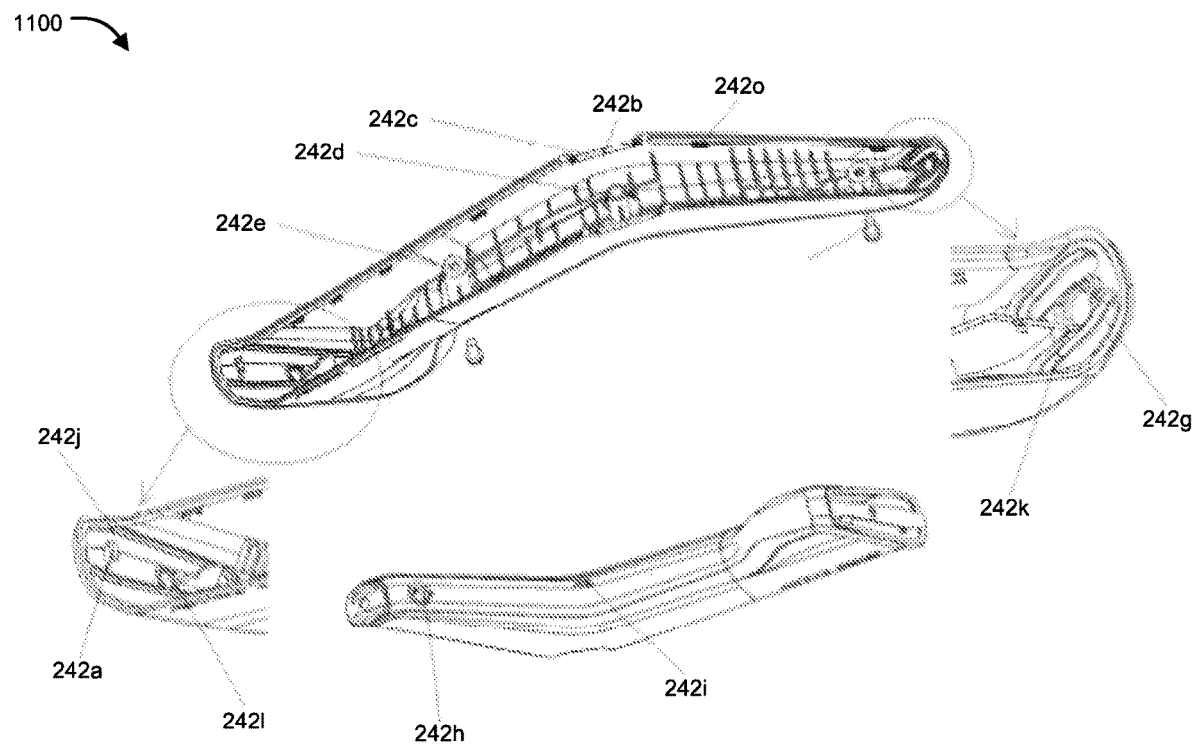
FIG. 11 illustrates bottom cover for the proposed device in accordance with embodiments of the present disclosure.

FIG. 11 illustrates bottom cover for the proposed device 200 in accordance with embodiments of the present disclosure. Bottom cover can include snaps 242a that can act a san integral component of the body of the bottom cover and used for clamping purpose fitted with the top cover snap 202a. Bottom cover screw clamping boss 242e can be provided for mounting of bottom cover clamping screw 242f with top cover 202. Hand wheel locating boss 242b can be provided for accurate location of hand wheel 220, and can be located with hand wheel locator and guiding slots 220c. Hand wheel opening slot 242c can be provided for hand wheel 220 opening through the bottom cover for manually operating it. Hollow boss 242d can be provided for locating the hand wheel shaft 220b, divergent side electrode mounting face 242l. Convergent side electrode mounting face 242g can be provided in the bottom cover for mounting of convergent side and divergent side electrodes (232, 238). For USB charging, opening slot 242*i* can be provided in the bottom cover 242. Screw cover can be fitted in the bottom cover 242 for covering the opening of screw 216. Bottom cover snaps 242*m* can be provided for snap grooves 202*b*. Convergent side electrodes 242*k* can be provided and an opening cut 242*i* can be provided for USB charging port. Bottom cover clamping screw 242*f* mounting in bottom cover clamping boss 242*e* and can be clamped in screw clamping boss 202*c*.

Figure 12:
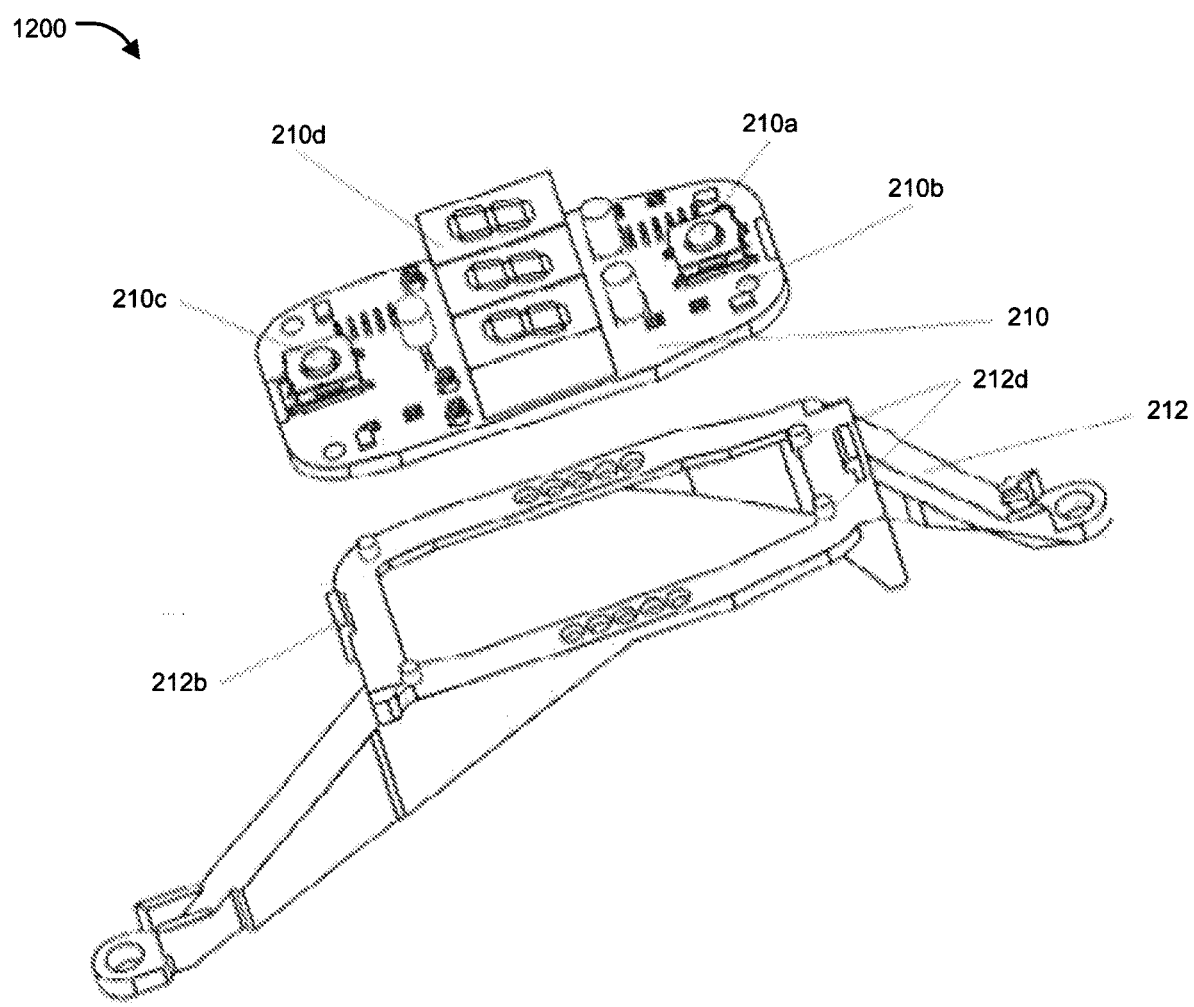
FIG. 12 illustrates an exemplary add-on PCB and bracket assembly device in accordance with an embodiment of the present disclosure.
Figure 13A:
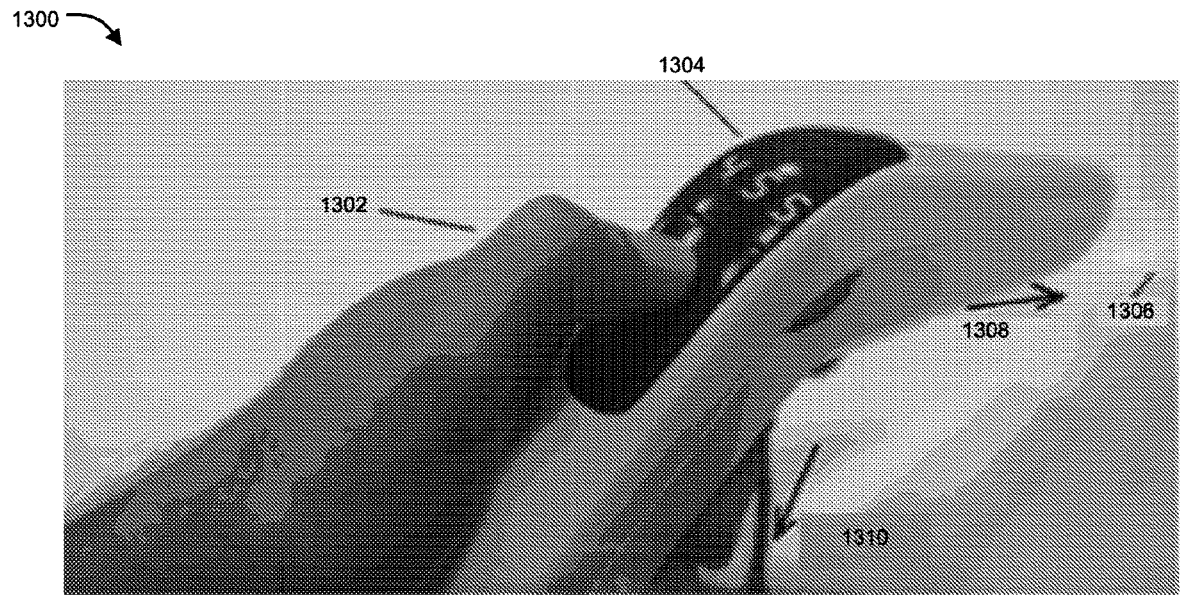
FIG. 13A illustrates an exemplary real time view of the proposed device being operated from convergent side in accordance with embodiments of the present disclosure.

FIG. 12 illustrates an add-on PCB and bracket assembly device in accordance with embodiments of the present disclosure. Add-on PCB brackets 212 can be mounted on top cover 202 through a clamping boss 202*d* having a snaps 212*b* for clamping the add on PCB 210 and contains convergent side as well as divergent side operating switch 210*a*, 210*c*. Add on PCB 210 further contains a display 210*d* for indicating the intensity of power supplied, and time duration up to which low energy photonic laser can be operated, battery condition and other relevant parameters. Clamping screw 212*d* can be received in hollow boss 210*b* the display can be any type as known in the related art such as but not limited to OLED display, capacitive touch display, or LED display FIG. 13A illustrates real time view of device 200 being operated from convergent side in accordance with embodiments of the present disclosure. As shown in device image 1300, operator can operate the device by hands 1302. Current pulse intensity of the laser beams 1306 of convergent side 1308 can be displayed on the display unit 1304. While using convergent side for smaller area coverage of beams on patient's body, divergent side 1310 can be positioned in opposite direction.

In an exemplary embodiment, operating procedure for convergent side low energy photonic laser system includes pushing the fine switch buttons located in the top cover. The switch operates the convergent side operating switch mounted on add on PCB. On pushing the fine switch, internal main circuit starts working, wherein the main circuit supplies power from the battery to the convergent side electrodes and to the low energy photonic laser emitted diode simultaneously, and wherein intensity of supplied power can be changed through encoder interconnected with hand wheel through the encoder gear as well as hand wheel gear for changing the intensity of power supplied.

On rotating the hand wheel, the encoder can operate the transformer that can change the voltage supplied to the electrodes. The changed intensity can be displayed in the display screen in a digital form in the front of user operating the device. In an embodiment, the hand wheel can be freely rotational by 360 degrees.

At the convergent side, on supplying power from the battery, low energy photonic laser is emitted from the diode, and laser rays pass through concave lenses and gets converged on a smaller area. The laser rays penetrate inside the body of a patient, and cells present in the human body absorb the laser rays and effectively stimulate healing to enable rapid pain relief. At the same time, power supplied to the convergent side electrodes pulsate electric molecular high voltage low amperage current to pass. Due to the high voltage low amperage current, metabolic activity of viable cells in that area starts increasing and hence accelerates healing and rapid pain relief occurs.

Figure 13B:
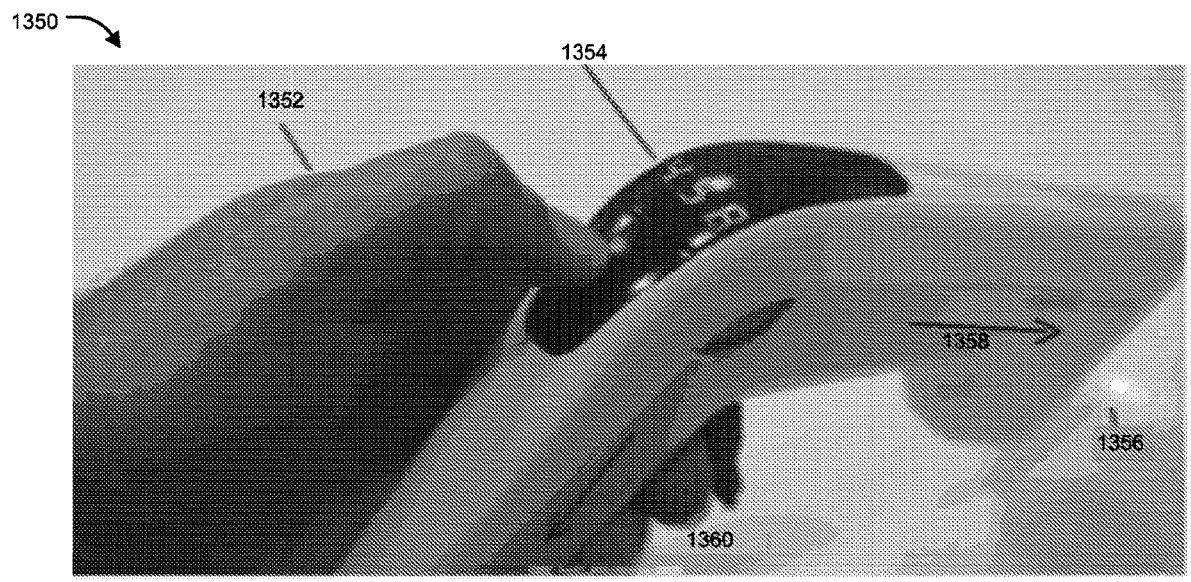
FIG. 13B illustrates an exemplary real-time view of device being operated from divergent side in accordance with embodiments of the present disclosure.

FIG. 13B illustrates real time view of device 200 being operated from divergent side in accordance with embodiments of the present disclosure. As shown in device image 1350, operator can operate the device by hand 1352. Current pulse intensity of the laser beams 1356 of divergent side 1358 can be displayed on the display unit 1354. While using divergent side for larger area coverage of beams on patient's body, convergent side 1360 can be positioned in opposite direction.

As is evident from FIGS. 13A and 13B, hand wheel projects out on both side of the device 200. Therefore, it is accessible for operation from either side. Thus, a user holding the device can operate the hand wheel using either his thumb or his index finger or both. Thus, the hand wheel can be operated with equal ease irrespective of whether held in left hand or right hand making it fit for ambidextrous application. For same reason, the hand wheel can be operated with equal ease irrespective of whether convergent side is being used or divergent side is being used. Besides above, the hand wheel can be freely rotational by 360 degrees.

Figure 14:
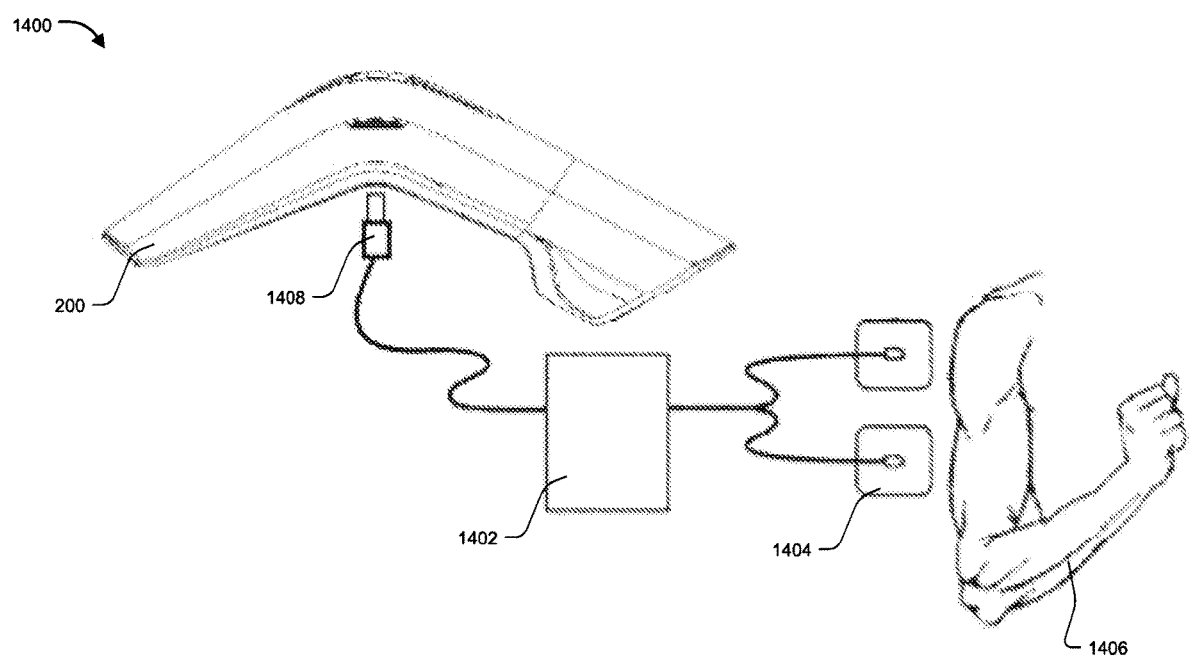
FIG. 14 illustrates an exemplary external electrode connection for typical user application scenario in accordance with embodiments of the present disclosure.

FIG. 14 illustrates an exemplary view showing external electrode connection for typical user application scenario in accordance with an embodiment of the present disclosure. Device 200 can be used to provide external electric pulse stimulation for healing. For this, external electrodes 1404 can be connected with external power source 1402 for generating pulse. External system can be connected with the disclosed device 200 through USB connector 1408 for controlling, monitoring & transferring the external system parameters. Negative and Positive electrodes 1404 are fixed on human skin 1406 where healing is required and USB Connector 1408 can be fixed in USB slot 222*a* of the device 200. It is to be appreciated that ability to operate the external electrodes as mentioned above can be helpful to a user in a way that the user will not have to hold the device for application. It also enables a user to take self-treatment on areas that cannot be reached by hand. The external electrodes can be patched on the skin of the user and the user can freely do his work without maneuvering the device. By placing such external electrode the user can also reach to areas of body where hand can be difficult to reach to give treatment.

In an exemplary embodiment, operating procedure for divergent side of the disclosed device 200 includes pushing a large switch button located on top cover on which internal main circuit starts working. Thereafter operating a divergent side operating switch mounted on the add on PCB power gets supplied from the battery to the divergent side electrodes, heaters, UV lights and to the low energy photonic laser emitted diode simultaneously. There can be switches to put on and off any of the four therapies depending on requirement. Intensity of the supplied power can be changed using hand wheel that is connected to encoder. On rotating the hand wheel, encoder operates the transformer and changes the voltage supplied to the electrodes as per the requirement. The changed intensity can be displayed in the display screen in a digital form visible to operator. At the divergent side, after supplying the power from battery, laser rays are emitted from the diode and passed through convex lenses to get diverged so as to focus at the larger area. The rays penetrate inside the body where cells absorb these laser rays such that the rays effectively stimulate healing to enable rapid pain relief. At the same time, depending on selection made, power also gets supplied to the divergent side electrodes, or heaters or UV emitters, on which respective therapies also get activated.

The disclosed device 200 can likewise be operated for use of convergent side holding the device from the divergent side.

The present disclosure therefore uses a combined/synergistic effect of laser along with other therapies, which has not been taught in any prior art. It is to be appreciated that a single device incorporating different therapies provides a cost effective alternative to different devices for individual therapies which if summed up are much more expensive. Besides, a device combining different therapies allows a user to use combination of different therapies enabling him to experience much more efficient healing response as compared to using a single therapy.

Furthermore, the disclosed therapeutic device is portable and yet has capability to provide any one or a combination of different therapies. It has been constructed such that it can be operated with either of left hand or right hand for operation of any of the first end and the second end, and therefore is configured to work efficiently for ambidextrous application.

While the foregoing describes various embodiments of the invention, other and further embodiments of the invention may be devised without departing from the basic scope thereof. The scope of the invention is determined by the claims that follow. The invention is not limited to the described embodiments, versions or examples, which are included to enable a person having ordinary skill in the art to make and use the invention when combined with information and knowledge available to the person having ordinary skill in the art.

ADVANTAGES OF THE INVENTION

The present disclosure provides a cost effective alternative for individual devices for individual therapies which if summed up are much more expensive.

The present disclosure provides a multifunctional therapeutic device that enables application to a large area or small area of human body.

The present disclosure provides a double ended therapeutic device that cater to small area and large area respectively.

The present disclosure provides a multifunctional therapeutic device that enables a user to use more than one therapy in different combinations for more efficient healing.

The present disclosure provides a multifunctional therapeutic device that incorporates means for any one or a combination of different therapies such as electric pulse therapy, U.V. therapy, Low energy laser therapy, and heat therapy to a human body part, thus making it a holistic therapeutic device.

The present disclosure provides a therapeutic device that is portable and yet has capability to provide any one or a combination of different therapies.

The present disclosure provides a therapeutic device that enables therapy through external electrodes.

The present disclosure provides a therapeutic device that is ambidextrous.

The present disclosure provides a therapeutic device that incorporates wireless connectivity to enable uploading/downloading of therapeutic data as well as remote control of the device.

We claim:

1. A multifunctional therapeutic device, the device comprising:
a first end configured for providing therapy to a smaller area of human body; and
a second end configured for providing therapy to a larger area of human body;
wherein each of the first end and the second end incorporates means for providing a plurality of therapies.

2. The device as claimed in claim 1, wherein the plurality of therapies include electric pulse therapy, UV therapy, Low energy laser therapy, and heat therapy.

3. The device as claimed in claim 2, wherein each of the first end and the second end incorporates capability to impart each of the plurality of therapies either individually or in any combination.

4. The device as claimed in claim 2, wherein each of the first end and the second end incorporates an identical laser source; and wherein the laser therapy to a smaller area by the first end and the laser therapy to a larger area by the second end is enabled by providing a set of converging lenses at the first end and a set of diverging lenses at the second end.

5. The device as claimed in claim 2, wherein the device is configured to be held from side of the second end for providing therapy using the first end, and to be held from side of the first end for providing therapy using the second end.

6. The device as claimed in claim 5, wherein the device includes a single display for displaying intensity of the plurality of therapies provided by the first end or the second end.

7. The device as claimed in claim 6, wherein the single display is positioned to be visible in either application by holding from side of the second end or by holding from side of the first end.

8. The device as claimed in claim 7, wherein the display in the single display rotates depending on which side is being used for providing the therapy.

9. The device as claimed in claim 6, wherein the device incudes an encoder to change the intensity of the therapy, and the encoder is operated by a hand wheel.

10. The device as claimed in claim 9, wherein the hand wheel is freely rotational by 360 degrees, and projects out on both sides of the device to be accessible for operation by thumb or by a finger or by both thumb and the finger of a user; and thus the hand wheel is configured to be operable irrespective of whether the device is used with left hand or right hand for operation of the first end or the second end.

11. The device as claimed in claim 1, wherein the device incorporates means for wireless communication.

12. The device as claimed in claim 11, wherein the device is configured to transfer therapy data to external devices using the wireless communication means.

13. The device as claimed in claim 11, wherein the device using the wireless communication means, is configured to receive data from any external communication platform for security, safety, upgrade of firmware, and for remotely controlling the device function.

14. The device as claimed in claim 2, wherein each of the first end and the second end incorporates a set of electrodes for enabling electric pulse therapy from each of the first end and the second end.

15. The device as claimed in claim 14, wherein the sets of electrodes for enabling electric pulse therapy at the first end and the second end also enable heat therapy when the respective end is being used for the therapy.

16. The device as claimed in claim 15, wherein a set of heaters is positioned behind each of the sets of the electrodes for use of the sets of electrodes for heat therapy.

17. The device as claimed in claim 2, wherein each of the first end and the second end incorporates a set of UV light emitters to enable the UV therapy from each of the first end and the second end.

18. The device as claimed in claim 2, wherein the device is configured for controlling, monitoring & transferring parameters to an external power source for a set of external electrodes fixed to a user's skin to provide external electric pulse stimulation for healing.

* * * * *